United States Patent [19]

Mixson et al.

[11] Patent Number: Plant 6,922

[45] Date of Patent: Jul. 11, 1989

[54] ST. AUGUSTINE GRASS '6-72-130-'

[75] Inventors: Wayne C. Mixson, Apopka, Fla.; Terrance P. Riordan, Lincoln, Nebr.; Virgil D. Meier, Marysville, Ohio

[73] Assignee: The O.M. Scott & Sons Company, Marysville, Ohio

[21] Appl. No.: 185,524

[22] Filed: Apr. 25, 1988

[51] Int. Cl.[4] ..... A01H 5/00

[52] U.S. Cl. ..... Plt./88

[58] Field of Search ..... Plt./88

*Primary Examiner*—James R. Feyrer

[57] ABSTRACT

A perennial St. Augustine grass with purple anthers and purple stigmas having good turf performance, good cold tolerance, short internodes and leaves and good resistance to gray leaf spot.

1 Drawing Sheet

BACKGROUND

A St. Augustine grass which has been named "Seville" was disclosed in U.S. Plant Pat. No. 4,097, which issued on Sept. 6, 1977. Another St. Augustine grass which has been named "Delmar" was disclosed in U.S. Plant patent application Ser. No. 893,960, filed Aug. 7, 1986. A further St. Augustine grass designated 6-72-182 is disclosed in U.S. Plant patent application Ser. No. 07/185,523, filed of even date herewith.

SUMMARY OF THE VARIETY

The present invention relates to a new and distinct perennial St. Augustine grass selected from the progeny of a controlled pollination of a plant originating in Florida with the pollen of a cold tolerant selection obtained from Memphis, Tenn. This purple anther, purple stigma genotype was labeled 6-72-130 and propagated vegetatively by stolons to provide planting stock for studying performance and making comparisons to present commercial varieties.

The combination of purple stigma, purple anthers, short internode length, short leaf blade length, good cold tolerance, a high tendency for purple stems, and good resistance to gray leaf spot of 6-72-130 along with other information allow this genotype to be distinguished from other St. Augustine grasses.

DETAILED DESCRIPTION OF THE VARIETY

Figure 1:
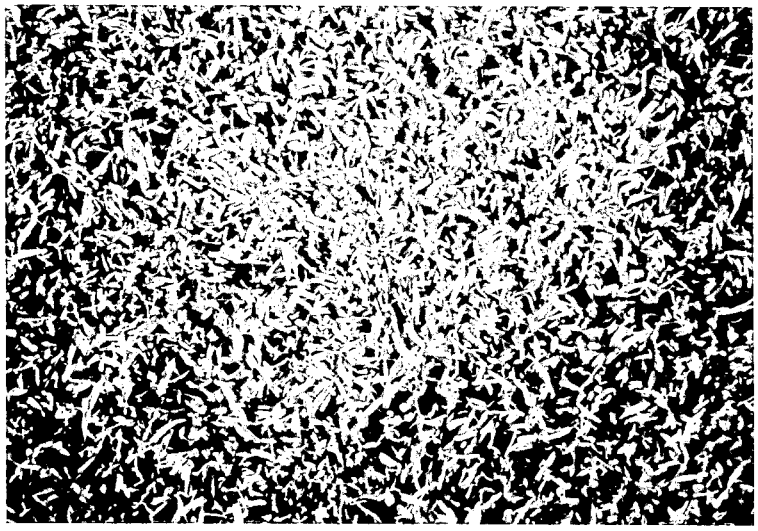
FIG. 1 is a photograph of 6-72-130 St. Augustine turf.
Figure 2:
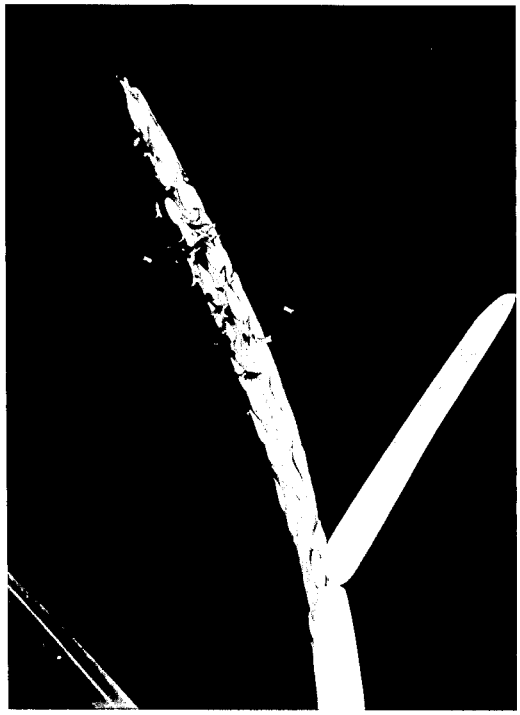
FIG. 2 shows a single spike of a 6-72-130 St. Augustine grass plant depicting purple anthers and purple stigmas protruding from several spikelets.
Figure 3:
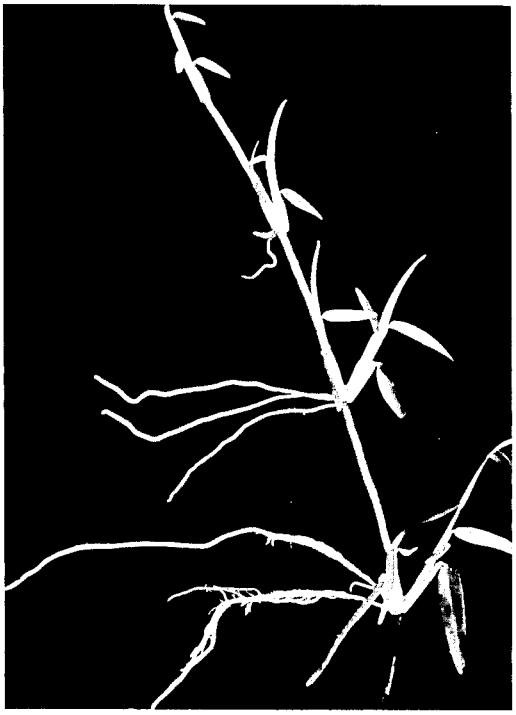
FIG. 3 is a photograph of a vegetative stolon of 6-72-130 St. Augustine grass.

Genotype 6-72-130 has a purple anther color, a purple stigma color, and an unreduced chromosome number of 18. The internodes are shorter and flatter than most St. Augustine varieties. Leaf blade measurements show that 6-72-130 generally has a shorter and narrower leaf blade than most varieties. From the standpoint of judging turf performance, the combination of shorter internodes, narrower leaf blades and shorter leaf blades results in a turf that is generally more dense, finer textured and produces fewer clippings. Measurements of the spike and related structures indicate that 6-72-130 has a shorter and narrower spike, a shorter and narrower peduncle, an average length but narrower flag leaf and a shorter flag leaf sheath than other St. Augustine grasses. The chromosome numbers, anther and stigma color and morphological measurements of 6-72-130 and other St. Augustine grasses are compared in Tables 1–4.

TABLE 1

Chromosome numbers, anther color, and stigma color of 6-72-130 and other St. Augustine grasses.

| Selection/Variety | Chromosome Number | Anther Color | Stigma Color |
|---|---|---|---|
| 6-72-130 | 18 | Purple | Purple |
| 6-72-182 | 18 | Yellow | White |
| Bitterblue | 27 | Yellow | Purple |
| Delmar | 18 | Yellow | White |
| Floratam | 27 | Yellow | Purple |
| Floratine | 27 | Yellow | Purple |
| Raleigh | 18 | Yellow | White |
| Seville | 18 | Yellow | Purple |
| Texas Common | 18 | Yellow | White |
| Caliifornia Common | 18 | Yellow | White |
| 1081 | 18 | Purple | Purple |

TABLE 2

Comparatiive measurements of internode length and thickness of 6-72-130 and other St. Augustine grasses.

| Selection/ Variety | No. of Nodes[a] | Internode[b] Length (cm) | Diameter (mm)[c] Longest | Shortest | Flat[d] |
|---|---|---|---|---|---|
| 6-72-130 | 5.2 | 5.6 | 2.7 | 1.9 | 1.44 |
| 6-72-182 | — | 4.8 | 2.8 | 2.2 | 1.32 |
| Bitterblue | — | 6.9 | 2.7 | 2.1 | 1.30 |
| Delmar | 4.5 | 5.7 | 3.5 | 2.6 | 1.35 |
| Floratam | 4.1 | 7.5 | 3.2 | 2.5 | 1.25 |
| Floratine | — | 5.8 | 2.7 | 2.2 | 1.30 |
| Raleigh | 4.5 | 7.0 | 3.2 | 2.5 | 1.27 |
| Seville | 4.8 | 6.8 | 2.7 | 2.2 | 1.25 |
| Texas Common | 4.4 | 6.2 | 3.0 | 2.2 | 1.35 |
| California Common | — | 4.2 | 2.4 | 2.0 | 1.22 |
| 1081 | — | 7.3 | 2.8 | 2.0 | 1.38 |
| LSD (.05) | — | 1.15 | 0.24 | 0.27 | 0.091 |

[a]Number of nodes per six inch stolon at Cleveland, Texas.

[b]Greenhouse planting at Marysville, Ohio. Measurements taken on unclipped potted plants using third internode from terminal end of stolon.

[c]Diameter measurements taken at the approximate center of the internode which has an elliptical shaped cross section.

[d]Flatness index equals longest axis divided by shortest axis. A larger flatness indicates a flatter shaped stem.

TABLE 3

Comparative Leaf Blade Lenght, Width and Sheath Length of 6-72-130 and other St. Augustine grasses.

| Selection/ Variety | Blade Length (cm) Texas[a] | Ohio[b] High[c] Light | Ohio[b] Low[d] Light | Blade width[c] (cm) Ohio[b] | Sheath Length[c] (cm) Ohio[b] |
|---|---|---|---|---|---|
| 6-72-130 | 2.2 | 5.2 | 14.8 | 1.3 | 2.7 |
| 6-72-182 | — | 5.3 | 13.7 | 1.5 | 2.3 |
| Delmar | 3.0 | 7.3 | 16.7 | 1.8 | 3.3 |
| Bitterblue | — | 7.4 | 17.5 | 1.5 | 2.8 |
| Floratam | 6.6 | 10.1 | 27.2 | 1.7 | 4.5 |
| Floratine | — | 8.6 | 16.3 | 1.4 | 3.2 |
| Raleigh | 3.9 | 7.8 | 13.8 | 1.7 | 3.7 |
| Seville | 2.9 | 6.9 | 18.4 | 1.4 | 2.9 |
| Texas Common | 2.7 | 8.1 | 16.6 | 1.7 | 3.6 |
| California Common | — | 3.8 | 11.8 | 1.2 | 2.2 |
| 1081 | — | 7.8 | 15.2 | 1.5 | 3.2 |
| LSD (.05) | .77 | 2.03 | 3.25 | 0.17 | 0.71 |

[a]Field Planting - Cleveland, Texas.
[b]Greenhouse Planting - Marysville, Ohio. Measurements taken on unclipped potted plants.
[c]After a period of natural sunlight and a high level supplemental light.
[d]After a lenghty period of very cloudy conditions and no supplemental light.

TABLE 4

Comparative measurements of the inflorescence and related structures of 6.72-130 and other St. Aufustine grasses[a].

| Selection/Variety | Spike Length (mm) | Spike Width (mm) | Peduncle Length (mm) | Peduncle Width (mm) |
|---|---|---|---|---|
| 6-72-130 | 56 | 4.8 | 41 | 1.7 |
| 6-72-182 | 60 | 4.3 | 52 | 1.6 |
| Delmar | 93 | 5.3 | 68 | 2.1 |
| Bitterblue | 78 | 5.6 | 61 | 2.2 |
| Floratam | 96 | 5.9 | 83 | 2.4 |
| Floratine | 74 | 5.8 | 48 | 2.3 |
| Raleigh | 72 | 5.8 | 62 | 2.2 |
| Seville | 71 | 4.9 | 50 | 1.9 |
| Texas Common | 68 | 4.9 | 42 | 1.9 |
| 1081 | 78 | 5.2 | 60 | 1.9 |
| LSD (.05) | 10.0 | .64 | 18.3 | 0.28 |

| Selection/Variety | Flag Leaf Length (mm) | Flag Leaf Width (mm) | Flag Leaf Sheath Length (mm) |
|---|---|---|---|
| 6-72-130 | 30 | 5.9 | 31 |
| 6-72-182 | 16 | 6.0 | 30 |
| Delmar | 21 | 6.7 | 46 |
| Bitterblue | 22 | 6.4 | 44 |
| Floratam | 35 | 6.3 | 46 |
| Floratine | 27 | 7.2 | 39 |
| Raleigh | 25 | 7.5 | 42 |
| Seville | 15 | 5.8 | 38 |
| Texas Common | 29 | 7.1 | 39 |
| 1081 | 25 | 6.3 | 39 |
| LSD (.05) | 12.4 | 1.08 | 6.7 |

[a]Greenhouse planting -i Marysville, Ohio.

Field observations of 6-72-130 indicate that it has generally good turf quality characteristics throughout the year and across the area of the United States where St. Augustine grass is adapted. It performs especially well in the climate of southern California. Although it performs best during the hotter summer months, it has good cold tolerance and performs well during the winter months. These characteristics of 6-72-130 as compared with other St. Augustine grasses are illustrated in Tables 5–7.

TABLE 5

Comparative turf quality[a] of 6-72-130 and other St. Augustine grasses at various locations in the U.S.

| Selection/Variety | Turf Quality Florida[b] Summer | Florida[b] Winter | Florida[b] Mean | California[c] | Texas[d] |
|---|---|---|---|---|---|
| 6-72-130 | 8.2 | 7.6 | 7.8 | 7.9 | 7.0 |
| 6-72-182 | 9.3 | 8.3 | 8.7 | — | — |
| Bitterblue | 7.3 | 5.9 | 6.0 | — | — |
| Calif. Common | — | — | — | 6.7 | — |
| Delmar | 9.8 | 9.0 | 9.6 | 5.9 | 7.0 |
| Floratam | 7.5 | 5.8 | 6.1 | — | 6.3 |
| Floratine | 7.2 | 6.1 | 6.4 | — | — |
| Florida Common | 8.2 | 6.6 | 7.0 | — | — |
| Raleigh | 6.7 | 7.1 | 7.4 | — | 6.3 |
| Seville | 9.0 | 7.9 | 8.1 | 6.8 | 6.3 |
| Texas Common | 6.5 | 8.4 | 8.0 | 4.6 | 8.3 |
| 1081 | 8.7 | 6.8 | 7.3 | — | — |
| LSD (.05) | 0.45 | 0.99 | 0.88 | | 1.7 |

[a]Quality - rated 1–10, 10 = best.
[b]Test planted at Apopka, Florida
[c]Test planted at Somas, California
[d]Test planted at Cleveland, Texas

TABLE 6

Comparative turf quality[a] of 6-72-130 and other St. Augustine grass varieties at the South Coast Field Station of the University of California - Riverside.

| Selection/Variety | Turf Quality Summer | Winter | Mean |
|---|---|---|---|
| 6-72-130 | 6.6 | 4.6 | 5.4 |
| 6-72-182 | 5.8 | 4.5 | 5.0 |
| Calif. Common | 5.4 | 4.2 | 4.7 |
| Delmar | 5.3 | 4.7 | 4.9 |
| Floratam | 5.4 | 4.1 | 4.6 |
| Raleigh | 4.6 | 3.3 | 3.9 |
| Texas Common | 5.5 | 4.3 | 4.8 |
| LSD (.05) | 0.50 | 0.44 | 0.39 |

[a]Quality-rated 1–10, 10 = best.

TABLE 7

Comparative cold injury of 6-72-130 and other St. Augustine grasses in Apopka, Florida.

| Selection/Variety | Cold Injury (%) Expt. 1 | Expt. 2 | Expt. 3 | Expt. 4 | Mean |
|---|---|---|---|---|---|
| 6-72-130 | 35 | 17 | 38 | 18 | 27 |
| 6-72-182 | 21 | 5 | 35 | 28 | 22 |
| Bitterblue | 53 | 38 | 58 | 34 | 46 |
| Delmar | 0 | 0 | 17 | 3 | 5 |
| Floratam | 40 | 42 | 55 | 40 | 44 |
| Floratine | 48 | 32 | 37 | 26 | 36 |
| Raleigh | 32 | 12 | 37 | 24 | 28 |
| Texas Common | 18 | 7 | 33 | 28 | 21 |
| 1081 | 47 | 33 | 48 | 33 | 40 |
| LSD (.05) | 20.9 | 18.5 | 26.1 | 23.5 | 16.5 |

Color of turf is an important component of turf quality. 6-72-130 has a pleasant medium green color comparable to many other St. Augustine grasses. Other factors that have shown varietal differences include: tendency to turn brown during the winter, for which 6-72-130 is rated about average; susceptibility to Asulox (an important herbicide) to which 6-72-130 is not susceptible; tendency to have a flush of seedheads in the spring, for which 6-72-130 has a lower tendency than other varieties; purple stem color, especially during cold weather, for which 6-72-130 has a higher than average tendency; susceptibility to gray leaf spot to which 6-72-130 has good resistance; and susceptibility to chinch bugs to which 6-72-130 has shown no greater susceptibility than most other varieties. Data on turf color, winter browning, Asulox injury, seedheads, purple stems, gray leaf spot and chinch bugs are illustrated in Tables 8–12.

TABLE 8

Comparative color ratings of 6-72-130 and other St. Augustine grasses at various locations in the U.S.

| | Color[a] | | | |
|---|---|---|---|---|
| | Florida[b] | | California | |
| Selection/Variety | Summer | Mean | Scfs[c] | Somas[d] |
| 6-72-130 | 8.6 | 7.7 | 3.8 | 8.4 |
| 6-72-182 | 9.8 | 8.5 | 3.9 | — |
| Bitterblue | 8.5 | 7.6 | — | — |
| Calif. Common | — | — | 3.8 | 8.4 |
| Delmar | 10.0 | 8.9 | 4.6 | 8.2 |
| Floratam | 8.8 | 7.8 | 4.2 | — |
| Floratine | 8.0 | 7.5 | — | — |
| Florida Common | 8.3 | 7.9 | — | — |
| Raleigh | 7.0 | 6.5 | 3.4 | — |
| Seville | 9.2 | 8.5 | — | 7.2 |
| Texas Common | 6.8 | 7.9 | 4.0 | 6.3 |
| 1081 | 8.8 | 8.0 | — | — |
| LSD (.05) | 0.48 | 0.67 | 0.35 | |

[a]Color rated 1–10, 10 = darkest green.
[b]Test planted at Apopka, Florida.
[c]Test planted at South Coast Field Station, University of California - Riverside.
[d]Test planted at Somas, California.

TABLE 9

Comparative ratings of various attributes of 6-72-130 and other St. Augustine grasses which detract from overall appearance.

| Selection/Variety | Brown[a] | Asulox[b] | Seed Heads[c] |
|---|---|---|---|
| 6-72-130 | 6.3 | 5 | 7.7 |
| 6-72-182 | 5.0 | 0 | — |
| Delmar | 3.7 | 0 | 5.7 |
| Bitterblue | — | 12 | — |
| Floratam | 6.3 | 0 | 7.0 |
| Floratine | — | 2 | — |
| Raleigh | 8.3 | 10 | 3.0 |
| Seville | — | 3 | 5.7 |
| Texas Common | 5.7 | 0 | 5.7 |
| California Common | 4.0 | — | — |
| 1081 | — | 7 | — |
| LSD (.05) | 2.0 | 5.3 | 2.3 |

[a]Test planted at South Coast Field Station - University of California - Rated as % brown turf.
[b]Test planted at Apopka, Florida - Rated as % injury.
[c]Test planted at Cleveland, Texas - Rated 0–9, 9 = no seedheads, 1 = many seedheads.

TABLE 10

Comparative evaluations of purple stem color of 6-72-130 and other St. Augustine grasses.

| | Purple Stem Color[a] | | |
|---|---|---|---|
| Selection/Variety | Ohio[b] | Florida[c] | California[d] |
| 6-72-130 | 8.3 | 30 | 4.3 |
| 6-72-182 | 4.5 | 3 | 0 |
| Bitterblue | 8.0 | 10 | — |
| Cal. Common | — | — | 0.7 |
| Delmar | 3.5 | 7 | 0.7 |
| Floratam | 8.3 | 20 | 2.7 |
| Floratine | 8.0 | 8 | — |
| Raleigh | 6.0 | 28 | 1.7 |
| Seville | 4.0 | 0 | — |
| Texas Common | 4.5 | 8 | 1.0 |
| 1081 | 7.5 | 58 | — |
| LSD (.05) | 1.1 | 15 | 0.9 |

[a]Purple stem color rated 1–10, 10 = stolons are very purple, 1 = stolons are entirely green. For Florida, visual estimation of the level of stem purpling in percent.
[b]Test planted in the greenhouse at Marysville, Ohio.
[c]Test planted at Apopka, Florida.
[d]Test planted at South Coast Field Station, University of California - Riverside.

TABLE 11

Comparative ratings of gray leaf spot[a] of 6-72-130 and other St. Augustine grasses at Apopka, Florida.

| Selection/Variety | |
|---|---|
| 6-72-130 | 1.7 |
| 6-72-182 | 1.7 |
| Bitterblue | 3.5 |
| Delmar | 1.0 |
| Floratam | 3.8 |
| Floratine | 2.6 |
| Raleigh | 0.7 |
| Seville | 0.8 |
| Texas Common | 2.4 |
| 1081 | 2.2 |
| LSD (.05) | 0.8 |

[a]Rated 1–10, 10 = most disease.

TABLE 12

Comparative ratings of chinch bug tolerance[a] of 6-72-130 and other St. Augustine grasses.

| Selection/Variety | Florida[b] | California[c] |
|---|---|---|
| 6-72-130 | 1.7 | 0.5 |
| 6-72-182 | 3.0 | — |
| Delmar | 2.0 | 0.0 |
| Bitterblue | 5.0 | — |
| Floratam | 7.0 | — |
| Floratine | 2.7 | — |
| Raleigh | 6.3 | — |
| Seville | 5.7 | 0.3 |
| Texas Common | 4.7 | 2.0 |
| California Common | — | 3.0 |

[a]Rated 1–10, 10 = severe damage.
[b]Test planted in the greenhouse at Apopka, Florida.
[c]Test planted at the South Coast Field Station, University of California - Riverside.

What is claimed is:

1. A St. Augustine grass, substantially as herein illustrated and described.

* * * * *